United States Patent
Adsul et al.

(10) Patent No.: US 11,242,549 B2
(45) Date of Patent: Feb. 8, 2022

(54) BIO-REFINERY WASTE UTILIZATION FOR ENZYME PRODUCTION USING NOVEL PENICILLIUM FUNICULOSUM MRJ-16 FUNGAL STRAIN

(71) Applicants: INDIAN OIL CORPORATION LIMITED, Maharashtra (IN); DEPARTMENT OF BIOTECHNOLOGY, New Delhi (IN)

(72) Inventors: Mukund Adsul, Faridabad (IN); Simranjeet Kaur Sandhu, Faridabad (IN); Reeta Rani Singhania, Faridabad (IN); Ravi Prakash Gupta, Faridabad (IN); Suresh Kumar Puri, Faridabad (IN); Sankara Sri Venkata Ramakumar, Faridabad (IN); Anshu Shankar Mathur, Faridabad (IN); Deepak Kumar Tuli, Faridabad (IN)

(73) Assignees: INDIAN OIL CORPORATION LIMITED, Mumbai (IN); DEPARTMENT OF BIOTECHNOLOGY, New Delhi (IN)

( * ) Notice: Subject to any disclaimer, the term of this patent is extended or adjusted under 35 U.S.C. 154(b) by 103 days.

(21) Appl. No.: 16/785,599

(22) Filed: Feb. 8, 2020

(65) Prior Publication Data
US 2020/0332329 A1    Oct. 22, 2020

(30) Foreign Application Priority Data

Apr. 17, 2019   (IN) .............................. 201921015449

(51) Int. Cl.
| | | |
|---|---|---|
| C12P 19/14 | (2006.01) | |
| C12N 9/42 | (2006.01) | |
| C12N 1/14 | (2006.01) | |
| C12R 1/80 | (2006.01) | |

(52) U.S. Cl.
CPC ............ *C12P 19/14* (2013.01); *C12N 9/2437* (2013.01); *C12N 1/145* (2021.05); *C12R 2001/80* (2021.05)

(58) Field of Classification Search
CPC ....... C12P 19/14; C12P 19/16; C12P 2201/00; C12P 21/02; C12N 9/2437; C12N 1/145; C12R 2001/80
See application file for complete search history.

(56) References Cited

U.S. PATENT DOCUMENTS

| | | |
|---|---|---|
| 9,249,402 B2 | 2/2016 | Ben Chaabane et al. |
| 2011/0262997 A1 | 10/2011 | Smith et al. |
| 2014/0045227 A1 | 2/2014 | Rarbach et al. |

OTHER PUBLICATIONS

Maeda, R. N., "Cellulase production by Penicillium funiculosum and its application in the hydrolysis of sugar cane bagasse for second generation ethanol production by fed batch operation," Journal of Biotechnology, vol. 163, No. 1, pp. 38-44 (2013).
De Castro, A. M., "Cellulases from Penicillium funiculosum: production, properties and application to cellulose hydrolysis," Journal of Industrial Microbiology & Biotechnology, vol. 37, No. 2, pp. 151-158 (Feb. 2010).
Adsul, M. G., "Cellulases From Penicillium Janthinellum Mutants: Solid-State Production and Their Stability in Ionic Liquids," Bioresources, vol. 4, No. 4, pp. 1670-1681 (Nov. 2009).
Mishra, C., "Hydrolysis of lignocelluloses by penicillium funiculosum cellulase," Biotechnology and Bioengineering, vol. 26, No. 4, pp. 370-373 (Apr. 1984).

*Primary Examiner* — Louise W Humphrey
*Assistant Examiner* — Anjali Ajit Hirani
(74) *Attorney, Agent, or Firm* — Maschoff Brennan

(57) ABSTRACT

The present invention relates to a method for obtaining a high titer of enzyme mixture comprising cellulases, hemicellulases and β-glucosidases in reutilization of waste water generated during hot water extraction of lignocellulosic biomass or biorefinery waste water using *Penicillium funiculosum* MRJ-16 mutant strain. The cellulose or lignocellulosic biomass used in the fermentation process is selected from the group consisting of rice straw, wheat straw, corn stover, cotton stalk or a combination thereof. The enzyme mixture obtained by the present process is used for the saccharification of acid pretreated lignocellulosic biomass.

8 Claims, No Drawings

BIO-REFINERY WASTE UTILIZATION FOR ENZYME PRODUCTION USING NOVEL PENICILLIUM FUNICULOSUM MRJ-16 FUNGAL STRAIN

FIELD OF THE INVENTION

Present invention relates to a method for obtaining a high titer of enzyme mixture in reutilization of waste water generated during pretreatment of lignocellulosic biomass. More specifically, the present invention relates to a method for obtaining high titer of enzyme mixture comprising cellulases, hemicellulases and β-glucosidases in reutilization of waste water generated during pretreatment of lignocellulosic biomass using *Penicillium funiculosum* MRJ-16 mutant strain.

BACKGROUND OF THE INVENTION

Lignocellulosic biomass comprises of three main fractions; cellulose, hemicelluloses and lignins, varying in their composition and arrangement depending upon the crop type and environmental conditions. The process of transforming lignocellulosic biomass to ethanol generally comprises three steps: first pretreatment (acid, alkali or steam explosion) that make cellulose and hemicelluloses accessible to enzymes, second enzymatic hydrolysis of cellulose and hemicelluloses to release hexose and pentose sugars and third is utilization of pentose and hexose sugars by fermenting yeast to produce ethanol.

Pretreatment of lignocellulosic biomass can involve multiple steps like washing, soaking, chemical, high temperature, steam explosion etc. Most commonly used acid pre-treatment of lignocellulosic biomass aimed to increase the surface area of cellulose by hydrolyzing major fraction of hemicelluloses and small fraction of cellulose so that enzymes easily access the cellulose and release glucose. Acid pretreatment hydrolyze the hemicellulose fraction to release xylose, glucose, mannose and arabinose and depending upon the severity of treatment these sugars get converted into toxic substances such as hydroxyl methyl furfurals, formic acid, acetic acid and furfurals. Presence of these inhibitors negatively affects the growth of micro-organisms and enzyme action.

Enzymatic breakdown of cellulose and hemicelluloses exposed required various cellulases, hemicellulases and β-glucosidase enzymes. These enzymes are produced industrially by fungi belongs to genera *Trichoderma, Aspergillus* and *Humicola* sp. by submerged fermentation in either continuous or batch mode. On commercial scale fungal biomass is generally separated from the enzyme broth and clear enzyme broth is concentrated, formulated, stabilized and stored further use. For industrial purposes these fungal strains are mutagenize to improve its properties like high enzyme yield, high specific activity, minimum chemical requirement and versatility of enzymes.

US 2011/0262997 disclose a process of cellulases enzyme production by *Trichoderma reesei* in an economical way by using pre-treated lignocellulosic material as inducer. Fermentation was carried out for 165 h at 28° C. in Fed-Batch mode using soluble glucose as feed. Combined physical and chemical pre-treatment was given to corn stover. Pre-treatment was carried out at a pressure of about 450 psi at 235° C. using sulfuric acid (0.5-1.4%). However, the pre-treated material used was detoxified by washing, repeated soaking in water to remove compounds that inhibit the performance of microorganism. Detoxification method is time consuming, lot of water wastage and another additional cost factor to the overall process.

US 2016/9249402 disclose the production of cellulases and hemicellulases enzyme in two stages in which growth of fungus *Trichoderma reesei* CL847 occurs in batch mode for 50 h followed by continuous mode of enzyme production phase for more than 300 h in aerated stirred tank bioreactor. During enzyme production phase, inducer (acid pre-treated lignocellulosic hydrolysate containing soluble sugars) was added continuously at 8 ml/h of concentration. Acid pre-treated lignocellulosic hydrolysate was obtained from straw pre-treated by steam explosion with prior impregnation of sulfuric acid. The inducer solution used was not sterilized and no pH adjustment was done. The pH of fermentation media was controlled during entire process using 5.5M ammoniacal solution. The mass of the reaction was kept constant. The final productivity was 0.39 g/L/h with FPU of 77.6 IU/ml and β-glucosidase of 1.3 IU/mg. Although this process eliminates the need of hydrolysate pH rectification step and final productivity was high but β-glucosidase activity was low, which means the enzyme obtained will be incapable to efficiently hydrolyze the lignocellulosic biomass and extra β-glucosidase enzyme need to be added and thus the second generation ethanol production process lack competitiveness.

US 2014/045227 teach a process of efficient hydrolysis of lignocelluloses biomass and process integrated with enzyme production. Wheat straw was pretreated with sulphuric acid by hydrothermal treatment under pressure. Biomass slurry obtained was divided into two parts: (a) one part was used for enzyme production with 8% w/v pretreated biomass and 2% corn steep liquor in media. Fermentation was carried out by *Trichoderma reesei* for 5 days. (b) Other part of pre-treated wheat straw slurry was hydrolysed by enzyme prepared above along with mechanically sheared fungal mycelia and unutilized biomass. Enzyme dosage used was 0.5% w/w (protein/pre-treated straw) along with β-glucoside enzyme from Novozyme was added at 2 cellobiose units/mg cellulases at 20% substrate loading. Maximum of 40 g/L of glucose yield was obtained after 72 hrs of hydrolysis. In this process, no details of enzyme activities were given, additional β-glucoside enzyme was added during hydrolysis and enzyme dosage is quite high, all these points makes this process unfeasible at industrial scale.

In comparison to the prior art, present invention is aimed at providing method of cellulases enzyme production at high titer using economical media components by novel *Penicillium funiculosum* MRJ-16 mutant strain that is catabolite derepressed and can tolerate high concentration of inhibitors. The novel *Penicillium funiculosum* MRJ-16 mutant strain is having 6.47 FPU/ml and 62 BGL (IU/ml) whereas *Penicillium funiculosum* NCIM 1228 (Parent strain) is having 3.5 FPU/ml and 22.1 BGL (IU/ml) activity hence, the novel *Penicillium funiculosum* MRJ-16 mutant strain possess enhanced enzyme activity as compared to cited arts. Present invention will help to bring down the production cost of bioethanol and make the production sustainable and competitive along with processing waste effluents generated during pretreatment.

SUMMARY OF THE INVENTION

The present provides a method for obtaining a high titer of enzyme mixture comprising cellulases, hemicellulases and β-glucosidases in reutilization of waste water, the process comprising the steps of:

(i) preparing fermentation media comprising ammonium sulphate (3-5 g/L), KH$_2$PO$_4$ (4-6 g/L), MgSO$_4$.7H$_2$O (0.5-1 g/L), CaCO$_3$ (2.5-5 g/L), Glycerol (2-3 g/L), Corn steep solids (25-35 g/L), carbon source (25-40 g/L), Tween-80 (1-2 ml/L) and waste water obtained during pre-treatment of lignocellulosic biomass or biorefinery waste water;

(ii) inoculating the media components of step (a) with 10% active liquid seed culture of *Penicillium funiculosum* MRJ-16;

(iii) subjecting the *Penicillium funiculosum* MRJ-16 culture of step (b) to fermentation in an aerated fermenter;

(iv) harvesting the enzyme broth after the fermentation process of step (c) and subjecting the broth to centrifugation to obtain the enzyme mixture.

In an embodiment of the present invention, the waste water used in step (i) contains waxes, proteins, phenolics and inhibitors.

In an embodiment of the present invention, inhibitors in the waste water are organic acid, phenol, hydroxyl methyl furfural (HMF), formic acid, acetic acid and furfural.

In an embodiment of the present invention, the carbon source in the fermentation media of step (a) is selected from the group consisting of cellulose, acid pretreated lignocellulosic biomass or a combination thereof.

In an embodiment of the present invention, the fermentation process is carried out at a temperature in the range of 25–35° C., pH in the range of 4-6, aeration in the range of 0.5-2.5VVM and dissolved oxygen above 30%.

In an embodiment of the present invention, the fermentation process is carried out for a time period of 80-110 hours.

In an embodiment of the present invention, cellulose or lignocellulosic biomass used in the fermentation process is selected from the group consisting of rice straw, wheat straw, corn stover, cotton stalk or a combination thereof.

In an embodiment of the present invention, the enzyme mixture obtained is used for the saccharification of acid pretreated lignocellulosic biomass.

DETAILED DESCRIPTION OF THE INVENTION

While the invention is susceptible to various modifications and/or alternative processes and/or solvent system, specific embodiment thereof has been shown by way of examples and will be described in detail below. It should be understood, however that it is not intended to limit the invention to the particular processes and/or temperature, pH, ratios, quantity and strains disclosed, but on the contrary, the invention is to cover all modifications, equivalents, and alternative falling within the spirit and the scope of the invention as defined by the appended claims.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particulars and all details set forth herein are used in the context of some embodiments and therefore should not be necessarily taken as limiting factors to the attached claims. The attached claims and their legal equivalents can be realized in the context of embodiments other than the ones used as illustrative examples in the description below.

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described.

The present invention provides a method for obtaining a high titer of enzyme mixture comprising cellulases, hemicellulases and β-glucosidases in reutilization of waste water by *Penicillium funiculosum* MRJ-16 (MTCC Accession No. 25142 and date of deposition is 12 Jun. 2017) using waste water generated during pretreatment of lignocellulosic biomass. The present invention also provides a method for the production of high titer of cellulases and hemicellulases enzymes using *Penicillium funiculosum* MRJ-16 using waste water generated during pretreatment of lignocellulosic biomass.

The present provides a method for obtaining a high titer of enzyme mixture comprising cellulases, hemicellulases and β-glucosidases in reutilization of waste water, the process comprising the steps of:

(i) preparing fermentation media comprising ammonium sulphate (3-5 g/L), KH$_2$PO$_4$ (4-6 g/L), MgSO$_4$.7H$_2$O (0.5-1 g/L), CaCO$_3$ (2.5-5 g/L), Glycerol (2-3 g/L), Corn steep solids (25-35 g/L), carbon source (25-40 g/L), Tween-80 (1-2 ml/L) and waste water obtained during pre-treatment of lignocellulosic biomass or biorefinery waste water;

(ii) inoculating the media components of step (a) with 10% active liquid seed culture of *Penicillium funiculosum* MRJ-16;

(iii) subjecting the *Penicillium funiculosum* MRJ-16 culture of step (b) to fermentation in an aerated fermenter;

(iv) harvesting the enzyme broth after the fermentation process of step (c) and subjecting the broth to centrifugation to obtain the enzyme mixture.

Waste water generated by hot water extraction of lignocellulosic biomass contains waxes, proteins and phenolics. Inhibitors are generated during acid pretreatment of lignocellulosic biomass. Inhibitors are organic acids and phenols such as hydroxyl methyl furfural (HMF), formic acid, acetic acid and furfural.

In an embodiment, the present invention provides a method for the production of high titer of cellulases and hemicellulases enzymes using low cost minimum media components such as waste effluents generated during pretreatment of lignocellulosic biomass or biorefinery wastewater along with hyper-cellulolytic variants of *Penicillium funiculosum* MRJ-16.

In an embodiment of the present invention, the waste water used in step (i) contains waxes, proteins, phenolics and inhibitors.

In an embodiment of the present invention, inhibitors in the waste water are organic acid, phenol, hydroxyl methyl furfural (HMF), formic acid, acetic acid and furfural.

In an embodiment of the present invention, waste water used in step (i) of the process containing up to 0.1% concentration of inhibitors is used for enzyme production.

In an embodiment of the present invention, the carbon source in the fermentation media of step (a) is selected from the group consisting of cellulose, acid pretreated lignocellulosic biomass or a combination thereof.

In an embodiment of the present invention, the fermentation process is carried out at a temperature in the range of 25–35° C., pH in the range of 4-6, aeration in the range of 0.5-2.5VVM and dissolved oxygen above 30%.

In an embodiment of the present invention, the fermentation process is carried out for a time period of 80-110 hours.

In an embodiment of the present invention, cellulose or lignocellulosic biomass used in the fermentation process is selected from the group consisting of rice straw, wheat straw, corn stover, cotton stalk or a combination thereof.

In an embodiment of the present invention, the enzyme mixture obtained is used for the saccharification of acid pretreated lignocellulosic biomass.

Following non-limiting examples are given by way of illustration for specific embodiments thereof and therefore should not be construed to limit the scope of the invention.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Example 1—Production of Enzymes Using Preparatory Media

Fermentation process was carried out using ammonium sulphate (3-5 g/L), $KH_2PO_4$ (4-6 g/L), $MgSO_4.7H_2O$ (0.5-1 g/L), $CaCO_3$ (2.5-5 g/L), Glycerol (2-3 g/L), Corn steep solids (25-35 g/L), cellulose (25-40 g/L) and Tween-80 (1-2 ml/L) dissolved in distilled water. Novel *Penicillium funiculosum* MRJ-16 mutant strain developed in the laboratory was used for the study. Sterilized media was inoculation with 10% active liquid seed culture of *Penicillium* mutant strain. After 96 hours of fermentation, the enzyme broth was harvested and clear enzyme broth was analyzed. The results obtained were 16.5 g/L of protein, 78 IU/ml of β-glucosidase and 7.2 FPU/ml of filter paper activity.

Example 2—Effect of Inhibitors on Enzyme Production

Cultivation of *Penicillium funiculosum* MRJ-16 mutant strain was conducted under conditions and media composition identical to example no. 1 along with inhibitors at different concentration. Inhibitors such as hydroxyl methyl furfural (HMF), formic acid, acetic acid and furfural which normally released during acid pretreatment of lignocellulosic biomass were used. Inhibitors have detrimental effect on enzyme production capability of the fungus but this novel strain used in present study has minimal effect on its enzyme production. The analytical results obtained after 120 hours of fermentation were shown in table 1. Results showed that waste water containing up to 0.1% concentration of all the inhibitors can be used for enzyme production.

TABLE NO. 1

Enzyme production in the presence of inhibitors

| S. No. | Inhibitors | Average FPA/ml |
|---|---|---|
| 1 | HMF (0.25%) | 6.07 |
| 2 | Furfural (0.25%) | 6.83 |
| 3 | Acetic acid (0.5%) | 6.49 |
| 4 | Formic acid (0.1%) | 6.87 |
| 5 | HFAF (0.05%) | 6.97 |
| 6 | HFAF (0.1%) | 5.78 |
| 7 | HFAF (0.2%) | 0.014 |
| 8 | Control | 7.43 |

*HFAF (all the inhibitors in equal percentage)

Example 3—Utilization of Waste Water for the Production of Enzymes

Cultivation and enzyme production from *Penicillium funiculosum* MRJ-16 mutant strain was carried out under the conditions and media components identical in example no. 1 except that the water used for media preparation was waste water obtained after hot water washing of rice straw. Water procured after hot water extraction of rice straw contains sand particles, free sugars, waxes, phenolics, protein and ash. After 96 hours of incubation, enzyme broth was harvested and filter paper activity was analyzed.

TABLE NO. 2

Utilization of waste water generated after rice straw pretreatment (Hot water extraction and acid pre-treatment) for enzyme production

| S. No. | Variables | Filter paper activity (FPA/ml) | Hemicellulases/ xylanase | B-glucosidases |
|---|---|---|---|---|
| 1 | Control | 7.57 | 190 | 60 |
| 2 | Extractive water | 7.54 | 178 | 55 |

Production of Enzymes Using Pre-Treated Biomass and Waste Water Together for Enzyme Production Enzyme production from *Penicillium funiculosum* MRJ-16 strain was performed using media components and conditions as described in example no. 1 except the cellulose was replaced with acid pre-treated rice straw. Pretreatment of rice straw was done at sulfuric acid concentration from 0.5-1.5% w/w, temperature 110-160° C. for 10-30 min. Slurry obtained after acid pre-treatment of rice straw containing inhibitors was used as such after pH rectification for enzyme production. After 120 hours of cultivation results obtained were 16.2 g/L of protein, 180 IU/ml of Xylanase/Hemicellulase, 65 IU/ml of β-glucosidase and 6.5 FPU/ml of filter paper activity.

Example 5—Hydrolysis of Pre-Treated Lignocellulosic Biomass

The efficiency of enzyme produced in example 4 was determined by its ability to hydrolyze and produce glucose from lignocellulosic biomass such as acid pretreated rice straw. Hydrolysis was performed at high substrate loading of acid pretreated biomass i.e. 15% at pH 4-5, 50 mM citrate buffer, temperature 50° C. with enzyme loading of 5 FPU/g enzyme loading of dry substrate. Sugars released were determined at regular interval of time by HPLC. Enzyme cocktail worked efficiently and leads to 60% glucan conversion in 48 hours.

We claim:

1. A method for obtaining an enzyme mixture comprising cellulases, hemicellulases and beta-glucosidases in re-utilization of waste water, the method comprising the steps of:
   (a) preparing fermentation media comprising 3-5 g/L ammonium sulfate, 4-6 g/L $KH_2PO_4$, 0.5-1 g/L $MgSO_4$-$7H_2O$, 2.5-5 g/L $CaCO_3$, 2-3 g/L glycerol, 25-35 g/L corn steep solids, 25-40 g/L carbon source, 1-2 ml/L polysorbate 80, and waste water obtained during pre-treatment of lignocellulosic biomass or biorefinery waste water;
   (b) inoculating the media of step (a) with a liquid seed culture of *Penicillium funiculosum* MRJ-16 of Microbial Type Culture Collection (MTCC) Accession Number 25142;
   (c) fermenting the *Penicillium funiculosum* MRJ-16 culture of step (b) in an aerated fermenter; and
   (d) harvesting an enzyme mixture after centrifuging the fermented culture broth of step (c).

2. The method as claimed in claim 1, wherein the waste water comprises waxes, proteins, phenolics and inhibitors.

3. The method as claimed in claim 2, wherein the inhibitors in the waste water are organic acid, phenol, hydroxyl methyl furfural (HMF), formic acid, acetic acid and furfural.

4. The method as claimed in claim 1, wherein the carbon source in the fermentation media of step (a) is selected from the group consisting of cellulose, acid pretreated lignocellulosic biomass, and a combination thereof.

5. The method as claimed in claim 1, wherein the fermentation process is carried out at a temperature in the range of 25-35° C., pH in the range of 4-6, aeration in the range of 0.5-2.5 WM, and dissolved oxygen above 30%.

6. The method as claimed in claim 1, wherein the fermentation is carried out for a time period of 80-110 hours.

7. The method as claimed in claim 4, wherein the cellulose or lignocellulosic biomass is selected from the group consisting of rice straw, wheat straw, corn stover, cotton stalk, and a combination thereof.

8. The method as claimed in claim 1, wherein the enzyme mixture obtained is used for the saccharification of acid pretreated lignocellulosic biomass.

* * * * *